US011209409B2

(12) United States Patent
Cunningham

(10) Patent No.: US 11,209,409 B2
(45) Date of Patent: Dec. 28, 2021

(54) BOTTLE WITH SENSORS FOR PROBING AND OPTIMIZING BOTTLING LINE PERFORMANCE

(71) Applicant: G3 Enterprises, Inc., Modesto, CA (US)

(72) Inventor: John Cunningham, Tracy, CA (US)

(73) Assignee: G3 Enterprises, Inc., Modesto, CA (US)

(*) Notice: Subject to any disclaimer, the term of this patent is extended or adjusted under 35 U.S.C. 154(b) by 0 days.

(21) Appl. No.: 16/370,425

(22) Filed: Mar. 29, 2019

(65) Prior Publication Data

US 2019/0302082 A1 Oct. 3, 2019

Related U.S. Application Data

(60) Provisional application No. 62/650,695, filed on Mar. 30, 2018.

(51) Int. Cl.
| | | |
|---|---|---|
| G01N 33/14 | (2006.01) |
| B65D 1/02 | (2006.01) |
| B65D 23/00 | (2006.01) |
| B65D 51/24 | (2006.01) |
| B65D 81/02 | (2006.01) |
| G01K 1/14 | (2021.01) |
| B65D 25/02 | (2006.01) |

(52) U.S. Cl.
CPC ............. *G01N 33/146* (2013.01); *B65D 1/02* (2013.01); *B65D 23/00* (2013.01); *B65D 25/02* (2013.01); *B65D 51/245* (2013.01); *B65D 81/02* (2013.01); *G01K 1/14* (2013.01); *B65D 2201/00* (2013.01)

(58) Field of Classification Search
CPC ........ G01N 33/146; B65D 1/02; B65D 23/00; B65D 51/245; B65D 81/02; B65D 25/02; B65D 2201/00; G01K 1/14
See application file for complete search history.

(56) References Cited

U.S. PATENT DOCUMENTS

| | | | | |
|---|---|---|---|---|
| 2006/0026971 | A1* | 2/2006 | Sharpe .................. | G01K 13/00 62/126 |
| 2014/0138276 | A1* | 5/2014 | Smith .................... | B65B 69/00 206/459.1 |
| 2015/0122688 | A1* | 5/2015 | Dias ..................... | A47G 19/025 206/459.1 |
| 2015/0301521 | A1 | 10/2015 | Byron et al. | |
| 2015/0307245 | A1* | 10/2015 | Puccini ................. | B65D 41/02 215/228 |
| 2017/0156540 | A1* | 6/2017 | Wheatley ............. | B67D 1/1238 |

* cited by examiner

*Primary Examiner* — Xin Y Zhong
(74) *Attorney, Agent, or Firm* — Goodwin Procter LLP

(57) ABSTRACT

A bottle with sensors for probing and optimizing bottling line performance is disclosed. According to one embodiment a bottle, comprises an outer layer and a reservoir tube inside the outer layer that connects a reservoir inside the outer layer to a neck of the bottle. The bottle has a battery inside the outer layer and one or more sensors powered by the battery.

21 Claims, 10 Drawing Sheets

BOTTLE WITH SENSORS FOR PROBING AND OPTIMIZING BOTTLING LINE PERFORMANCE

RELATED APPLICATIONS

This application claims priority to U.S. provisional patent application 62/650,695, filed Mar. 30, 2018, entitled "A BOTTLE WITH SENSORS FOR PROBING AND OPTIMIZING BOTTLING LINE PERFORMANCE" the entire disclosure, which is hereby incorporated by reference.

FIELD

The present disclosure relates in general to the field of industrial systems, and in particular, to a bottle with sensors for probing and optimizing bottling line performance.

BACKGROUND

Systems exist for filling and capping or corking of bottles to contain any variety of juices, beers, wines, ciders or other carbonated or non-carbonated liquids. However, these systems are often expensive, and often require a great number of components and have a high degree of complexity. Due to these factors, these complex and costly systems are generally purchased by companies or individuals looking to fill a large number of bottles and are generally only cost effective when these machines fill and bottle with minimal downtime and finished package defects.

In-line inspection and control systems for bottling lines can start with empty container checks and proceed through container rinsing, filling, fill-level inspection, in-line weight checking, closure application inspection, label application inspection, and final packaging. Inspections systems are typically stand-alone that operate with either push rejection devices or progressive diverters for a more gentle removal of bad product from the process. Inspection systems typically use cameras and sensors along the bottling and packaging line to assess the bottling process and packages being produced.

SUMMARY

A bottle with sensors for probing and optimizing bottling line performance is disclosed. According to one embodiment a bottle, comprises an outer layer and a reservoir tube inside the outer layer that connects a reservoir inside the outer layer to a neck of the bottle. The bottle has a battery inside the outer layer and one or more sensors powered by the battery.

The above and other preferred features, including various novel details of implementation and combination of elements, will now be more particularly described with reference to the accompanying drawings and pointed out in the claims. It will be understood that the particular methods and apparatuses are shown by way of illustration only and not as limitations. As will be understood by those skilled in the art, the principles and features explained herein may be employed in various and numerous embodiments.

BRIEF DESCRIPTION OF THE DRAWINGS

The accompanying drawings, which are included as part of the present specification, illustrate the various embodiments of the present disclosed system and together with the detailed description of the preferred embodiments given below serve to explain and teach the principles of the present disclosure.

Figure 1:
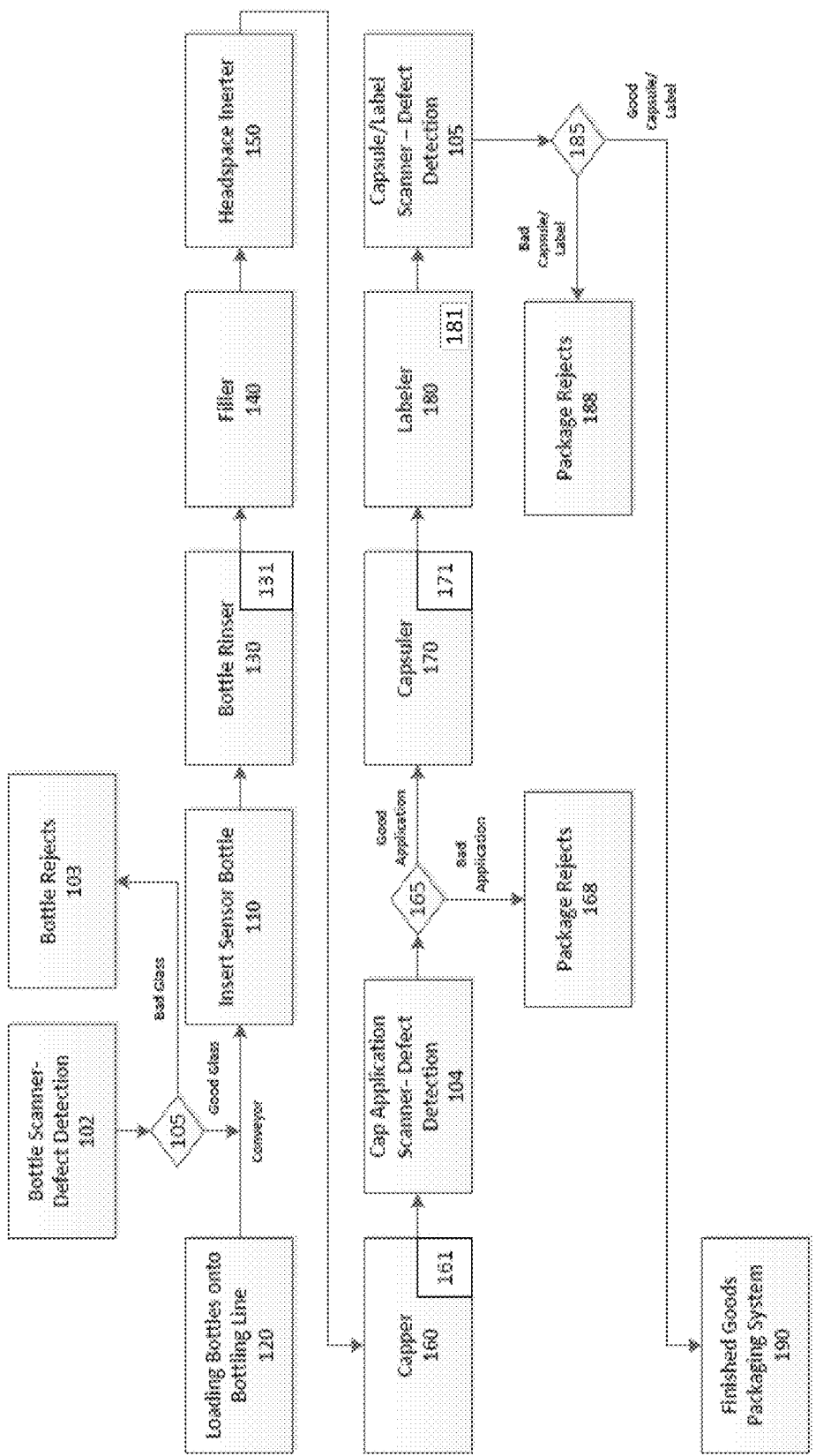
FIG. 1 depicts a screw-cap bottling line system for use with the present bottle, according to one embodiment.

It should be noted that the figures are not necessarily drawn to scale and that elements of structures or functions are generally represented by reference numerals for illustrative purposes throughout the figures. It also should be noted that the figures are only intended to facilitate the description of the various embodiments described herein. The figures do not describe every aspect of the teachings described herein and do not limit the scope of the disclosure.

DETAILED DESCRIPTION

A bottle with sensors for probing and optimizing bottling line performance is disclosed. According to one embodiment a bottle, comprises an outer layer acting as the bottle's body and an opening at the top allowing for a beverage to enter a tube inside the outer layer that connects to a reservoir inside the outer layer allowing the bottle to run through a rinser and/or filler. The bottle also has a battery or other energy source inside the outer layer and one or more sensors powered by the energy source.

The disclosure provides for a bottle with sensors ("the present bottle"), which collects data from various stages of a bottling line process train, such as a screw-cap bottling line operation applying screw-caps and a cork bottling line system inserting cork closures. By way of example only, the disclosed technology may be used for capping and corking bottling line set-ups, bottling line troubleshooting, and providing knowledge for predictive maintenance. Such systems can have the purpose of filling bottles with beverages, such as wines, sparkling wines, spirits, teas, coffees or nutraceuticals.

The present bottle allows for pre-bottling capper-head set-up, capper-head set-up confirmation, troubleshooting during commercial bottling runs, and prediction of equipment wear and potential break-downs or inefficiencies in the bottling line processes. Data from the present bottle alone or combined with bottling line data from other sources, such as; vision systems, fixed sensors installed in the various unit operations and PLC outputs may be used to create predictive mathematical models to further improve process set-ups, fault detection, troubleshooting, and predictive maintenance. Additionally, the generated data from any of these sources can be transmitted to a variety of systems including directly to a technician's smart device for immediate feedback during equipment set-up, directly to a gateway through wireless technologies and then to a technician's smart device or a processes controller for set-up and automated controls, and cloud storage systems, where additional analyses transformations and predictive analytics can be performed to create valuable recommendations for the bottling line mechanics, managers, and owners. These recommendations can be geared towards improving the bottling line's efficiency and profitability.

Figure 6:
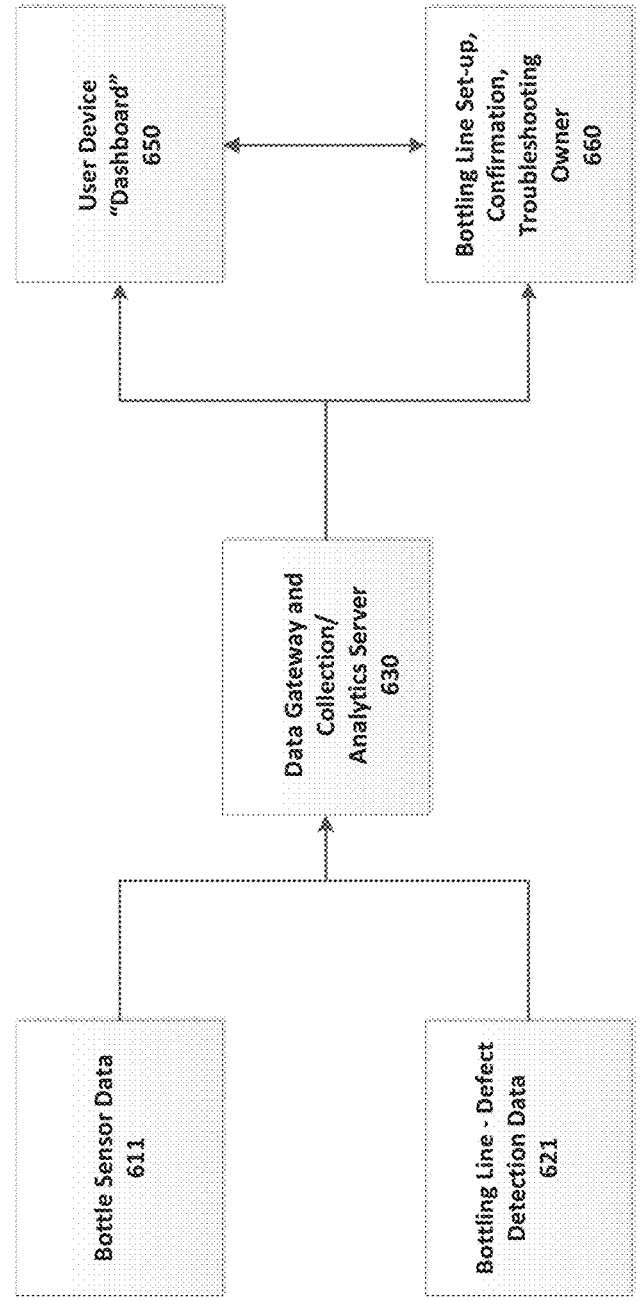
FIG. 6 depicts an exemplary network that collects and analyzes data from various sources including the sensor bottle, according to one embodiment.

FIG. 1 illustrates a screw-cap bottling line system 100, according to one embodiment. A screw-cap bottling line system 100 serves to fill containers, for example, glass bottles, with a beverage, such as wine, sparkling wine, or spirits. The screw-cap bottling line system 100 is outfitted with a bottle scanner defect detection system 102 that determines the bottle's fitness for use immediately after loading bottles onto bottling line 120. The data generated from the bottle scanner-defect detection system 102 can be transmitted, as depicted in FIG. 6, as bottling line-defect detection data 621 to a data gateway and collection/analytics server 630 for immediate feedback to the user via the user device dashboard 650 and for inclusion into predictive models. The present bottle 110 is transported on the screw-cap bottling line system 100 by a conveyance system (not shown). The present bottle 110 performs data collection functions at each step of the screw-cap bottling line system 100, and transmits that data for purposes of confirming that the bottling line set-up conditions are proper and providing input to predictive models used to generate crucial process information. The predictions from these analytics models are then sent to the proper devices and personnel, at the proper time, so actions can be taken to ensure that the screw-cap bottling line system 100 is functioning correctly and efficiently.

The present screw-cap bottling line system 100 includes an operation to load the empty bottles onto the bottling line 120, a bottle rinser 130, a filler 140, a headspace inerter 150, a capper 160, a capsuler 170, a labeler 180, and a finished goods packaging system 190, according to one embodiment. As the present bottle 110 is transported down the screw-cap bottling line 100, the present bottle 110 collects data, for example temperature, pressure, speed, vibrations, and chemical concentrations, and transmits that data for analysis, as described in more detail below.

The system to load the empty bottles onto the bottling line 120 involves transferring an empty bottle from a pallet or case to the line's conveyance system. In certain embodiments, the bottling line 120 is outfitted with a bottle scanner-defect detection system 102 that scans the bottles as they are being loaded onto the bottling line for finish characteristics such as sealing surface roughness, D—dimension (e.g., distance from top of neck to where pilfer is tucked under the glass), D—angle (e.g., the sharpness of the angle in the glass that the pilfer tucked is created), thread depth, bottle height, and cocked-neck. If any of these bottle characteristics measure outside of values that can be compensated for by process adjustments, the bottle is rejected to bottle rejects 103. In certain embodiments, during line setup or troubleshooting, the present bottle 110 is inserted into the conveyance system to collect vibration and G-force data as it is transported from its insertion location to the bottle rinser 130.

Figure 3:
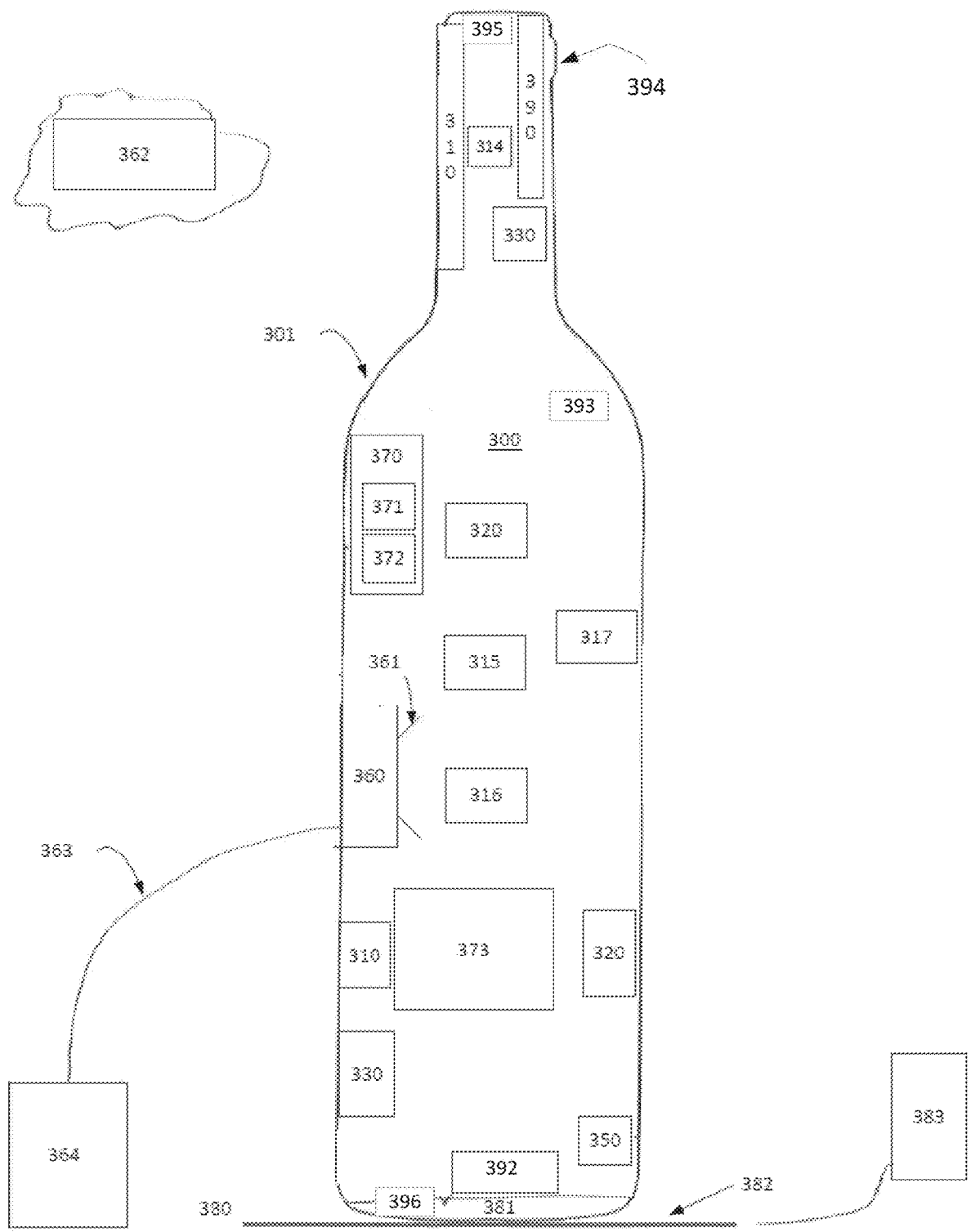
FIG. 3 depicts an exemplary sensor bottle, according to one embodiment.

The rinser 130 injects rinse solution into the present bottle 110, for example, to remove foreign material and help sanitize the bottle in preparation for filling it with the desired beverage. In certain embodiments, the present bottle 110 includes an internal pressure sensor 320, an internal temperature sensor 310, and an internal chemical sensor 330, as depicted in FIG. 3. The internal pressure sensor 320 measures the rinse solution pressure levels. The internal temperature sensor 310 serves to measure the temperature of the rinse solution 131. The internal chemical sensor 330 quantifies chemical property data, such as the pH of the rinse solution 131. The present bottle 110 is then transported to the filler 140.

The filler 140 applies a force to the top of the present bottle 110 to create a seal between the fill head and the bottle prior to dispensing a measured amount of a desired beverage, for example wine, into the present bottle 110. In certain embodiments, the force applied for this seal is measured by the force sensor 392. In certain embodiments, the internal pressure of the present bottle 110 is also measured by the internal pressure sensor 320. This force and pressure data is analyzed, to determine if the system is filling within the prescribed conditions for the beverage and bottles, since the filling process could be negatively impacted if the forces or pressures are improper. In one embodiment, the beverage fill height is measured by a level sensor 390 in the internal neck cavity of the present bottle 110. In certain embodiments, the present bottle 110 has an oxygen sensor 314 that measures the headspace oxygen concentration. In certain embodiments, the present bottle 110 has a sensor 316 in the internal body that measures the oxygen concentration, a pressure sensor 320 measuring internal bottle pressure and a temperature sensor 310 measuring the beverage temperature. In certain embodiments, the present bottle 110 includes a carbon dioxide sensor 315 to measure the amount of carbon dioxide contained in the beverage. The present bottle 110 is then transported through the headspace inerter 150 where the headspace oxygen sensor 314 senses the oxygen levels to ensure the inerting system is performing properly before moving to the capper system 160.

The capper system 160 applies a cap 161, which is made of a malleable metal such as aluminium, to the present bottle 110 by first applying a top load force to properly compress the cap liner. The capper system 160 then applies a thread roller force at the proper location to roll the malleable metal into the glass bottle's threads forming a grooved, tight, screw-like fit to the package. The capper system 160 then applies a pilfer roller force to tuck the cap 161 metal under a lip in the glass bottle allowing the cap's bridges to break and the skirt of the cap to remain on the bottle once the cap is removed by the consumer. This feature is important for providing consumers with pilfer evidence. In one embodiment, the measurements taken and recorded by the present bottle 110 include top-load force, thread roller position, thread roller force, pilfer roller position and pilfer roller force. In one embodiment, after the cap is applied, certain measurements are recorded by present bottle 110, such as the wine fill height, headspace oxygen concentration, and the wine's dissolved oxygen concentration allowing for the calculated estimate of the total package oxygen (TPO) that provides data to determine the quality of oxygen management in the filling, inerting and capping process.

At this stage of the screw-cap bottling line system 100, in certain embodiments, data regarding the cap application quality is generated by the cap application scanner-defect detection system 104. This system confirms a cap is installed properly by examining for and quantifying when possible reform depth, thread depth, thread start, thread runout, thread cuts, pilfer tuck, pilfer cuts and if possible, also checks/confirms the beverage fill height. In further embodiments, the cap application scanner-defect detection system 104 data can be combined with data previously collected by the present bottle 110 during line set-up or line troubleshooting and data collected by the bottle scanner-defect detection system 102 to predict if the package is of high enough quality to proceed to the capsuler 170 and to make recommendations regarding screw-cap bottling line system 100 adjustments required to improve performance. If the package is deemed defective it is sent to package rejects 168. If the data analytics indicates the package has acceptable quality it is cleared to proceed to the capsuler 170. The present bottle 110 is then transported to the capsuler 170.

The capsuler 170 applies a heat-shrink or roll-on capsule 171 to the neck of the present bottle 110, and applies heat or roller force to apply the capsule on the bottle's top. In one embodiment, the measurements taken and recorded by the present bottle 110 include temperature distributions and locations over time and roller forces and locations over time. The present bottle 110 is then transported to the labeler 180.

The labeler 180 involves applying a product label 181 to the body of the bottle using an adhesive, for example, the labeler 180 applies the product label 181 to the present bottle 110. In certain embodiments, the present bottle 110 has a sensor that measures the forces the bottling line exerts to apply the label to determine if the application is uniform. In certain embodiments, during production of the beverage package an external capsule/label scanner-defect detection system 105 measures and detects defects such as bubbles, wrinkles, or an uneven application of the heat-shrink/roll-on capsule 171 and the label 181. The external capsule/label scanner-defect detection system 105 also detects fish eyes that form due to moisture trapped under the capsule along with other defects such as burn marks or holes in the heat-shrink or roll-on capsule 171. In certain embodiments, during production of the beverage package the capsule/label scanner-defect detection system 105 scans the product label 181 for defects, such as wrinkles, scuffing, incorrect position, incorrect orientation, and flagging-edges, which can result from raw material or process issues. If defects exceed acceptable quality limits on the package, the package is sent to package rejects 188. During setup or troubleshooting the present bottle 110 is transported to finished goods packaging 190. All information regarding package defects can be sent to the user real-time and stored for future review including modelling. This information could include the number of rejects, the rate of rejects and the percent of total production rejected at any time.

The finished goods packaging 190 involves moving the present bottle 110 from the labeler 180 to packaging, which can include placing the finished product into a corrugated cardboard box. In certain embodiments, the present bottle 110 measures vibration and g-force data using internal 3-axis accelerometers 317 to detect excessively rough handling in the finished goods packaging 190 area. Data showing excessively rough handling would indicate that the system is set-up incorrectly, is malfunctioning, or the control parts are worn/broken.

Figure 2:
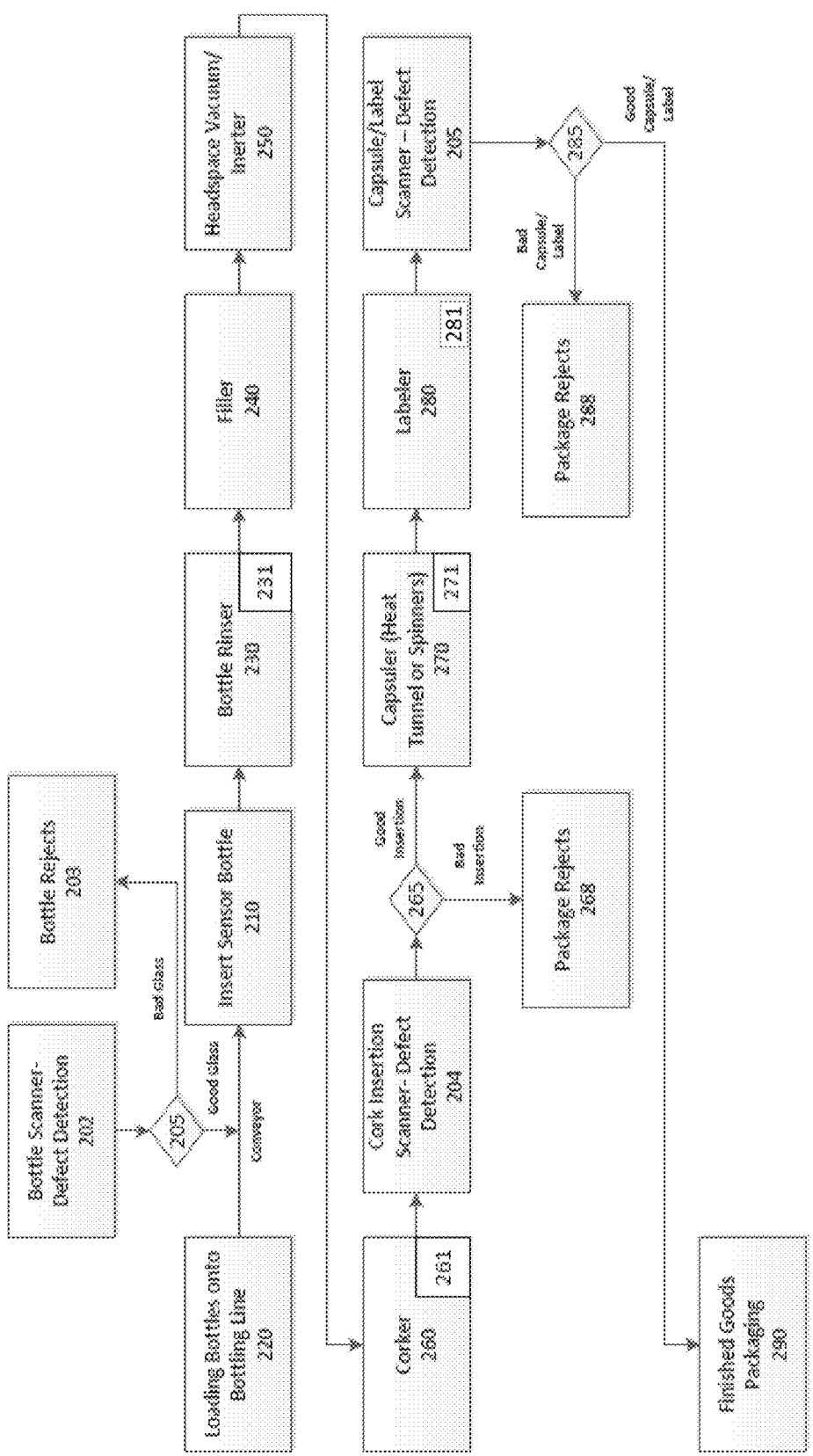
FIG. 2 depicts a cork closure bottling line system for use with the present bottle, according to one embodiment.

FIG. 2 illustrates a cork closure bottling line system 200, according to one embodiment. A cork closure bottling line system 200 serves to fill containers, for example, glass bottles, with a beverage, such as wine, sparkling wine, or spirits. The cork closure bottling line system 200 is outfitted with a bottle scanner defect detection system 202 that determines the bottle's fitness for use immediately after loading bottles onto bottling line 220. The data generated from the bottle scanner-defect detection system 202 can be transmitted, as depicted in FIG. 6, as bottling line-defect detection data 621 to a data gateway and collection/analytics server 630 for immediate feedback to the user via the user device dashboard 650 and for inclusion into predictive models. The present bottle 210 is transported on the cork closure bottling line system 200 by a conveyance system (not shown). The present bottle 210 performs data collection functions at each step of the cork closure bottling line system 200, and transmits that data for purposes of confirming that the bottling line set-up conditions are proper and providing input to predictive models used to generate crucial process information. The predictions from these analytics models are then sent to the proper devices and personnel, at the proper time, so actions can be taken to ensure that the cork closure bottling line system 200 is functioning correctly and efficiently.

The present cork closure bottling line system 200 is comprised of a system to load empty bottles onto bottling line 220, a bottle rinser 230, a filler 240, a headspace vacuum/inerter 250, a corker 260, a capsuler (heat tunnel or spinners) 270, a labeler 280, and a finished goods packaging 290, according to one embodiment. As the present bottle 210 is transported down the cork closure bottling line system 200, the present bottle 210 collects data, for example temperature, pressure, speed, vibrations and chemical data, and transmits that data for analysis, as described in more detail below.

The system to load the empty bottles onto the bottling line 220 involves transferring an empty bottle from a pallet or case to the line's conveyance system. In certain embodiments, the bottling line 220 is outfitted with a bottle scanner-defect detection system 202 that scans the bottles as they are being loaded onto the bottling line for finish characteristics such as the bottle bore profile, bottle height, and cocked-neck. If any of these bottle characteristics measure outside of values that can be compensated for in process adjustments, the bottle is rejected to bottle rejects 203. In certain embodiments, during line setup or troubleshooting, the present bottle 210 is inserted into the conveyance system to collect vibration and G-force data as it is transported from its insertion location to the bottle rinser 230.

The rinser 230 injects rinse solution into the present bottle 210, for example, to remove foreign material and help sanitize the bottle in preparation for filling with the desired beverage. In certain embodiments, the present bottle 210 includes an internal pressure sensor 320, an internal temperature sensor 310, and an internal chemical sensor 330, as depicted in FIG. 3. The internal pressure sensor 320 measures the rinse solution pressure levels. The internal temperature sensor 310 serves to measure the temperature of the rinse solution 231 The internal chemical sensor 330 quantifies chemical property data, such as the pH of the rinse solution 231. The present bottle 210 is then transported to the filler 240.

The filler 240 applies a force to the top of the present bottle 210 to create a seal between the fill head and the bottle prior to dispensing a measured amount of a desired beverage, for example wine, into the present bottle 210. In certain embodiments, the force applied for this seal is measured by the force sensor 392. In certain embodiments, the internal pressure of the present bottle 210 is also measured by the internal pressure sensor 320. This force and pressure data is analyzed, to determine if the system is filling within the prescribed conditions for the beverage and bottles, since the filling process could be negatively impacted if the forces or pressures are improper. In one embodiment, the beverage fill height is measured by a level sensor 390 in the internal neck cavity of the present bottle 210. In certain embodiments, the present bottle 210 has an oxygen sensor 314 that measures the headspace oxygen concentration. In certain embodiments, the present bottle 210 has a sensor 316 in the internal body that measures the beverage oxygen concentration, a pressure sensor 320 measuring the internal bottle pressure and a temperature sensor 310 measuring the beverage temperature. In certain embodiments, the present bottle 210 includes a carbon dioxide sensor 315 to measure the amount of carbon dioxide contained in the beverage. The present bottle 210 is then transported through the headspace vacuum/inerter 250 to the corker 260.

The corker 260 compresses and inserts a cork 261, which can be made from the bark of *Quercus suber*, (oak trees that produce corks wood used in natural cork closures), agglomerated cork, plastic materials, or other compounds formed into a proper cylindrical cork form, to the present bottle 210. This corking process involves centering the present bottle 210 under the cork locks, the cork locks compressing the cork to the proper diameter, and a push rod pushing the compressed cork into the present bottle 210 neck. The cork then expands from its compressed state to fill, and apply force to, the inside of the present bottle 210 neck. In one embodiment, the measurements taken and recorded by the present bottle 210 include the force of the expanding cork against the neck, the time it takes to achieve a steady-state force, and the insertion location of the cork in the present bottle 210 bottle. In one embodiment, after the cork insertion, certain measurements are recorded by present bottle 210, such as the fill height of the wine, headspace oxygen concentration, and the dissolved oxygen concentration in the wine allowing for the calculated estimate of total package oxygen ("TPO") that provides data to determine the quality of oxygen management in the filling, vacuum/inerting and corking process.

At this stage of the cork closure bottling line system 200, in certain embodiments, data regarding the cork insertion quality is generated by the cork insertion scanner-defect detection system 204. System 204 confirms that a cork is inserted properly by examining its top and bottom insertion depth and, if possible, also checks the beverage fill height. In further embodiments, the cork insertion scanner-defect detection system 204 data can be combined with data previously collected by the present bottle 210 during line set-up or line troubleshooting and data collected by the bottle scanner-defect detection system 202 to predict if the package is of high enough quality to proceed to the capsuler 270 and to make recommendations regarding cork closure bottling line system 200 adjustments required to improve performance. If the package is deemed defective it is sent to package rejects 268. If the data analytics indicates the package has acceptable quality it is cleared to proceed to the capsuler 270. The present bottle 210 is then transported to the capsuler 270.

The capsuler 270 applies a heat-shrink or roll-on capsule 271 to the neck of the present bottle 210, and applies heat or roller force to apply the capsule on the bottle's top. In one embodiment, the measurements taken and recorded by the present bottle 210 include temperature distributions and locations over time or roller forces and locations over time. The present bottle 210 is then transported to the labeler 280.

The labeler 280 involves applying the product label 281 to the body of the bottle using an adhesive, for example, the labeler 280 applies the product label 281 to the present bottle 210. In certain embodiments, the present bottle 210 has a sensor that measures the forces the bottling line exerts to apply the label 281 to determine if the application is uniform. In certain embodiments, during production of the beverage package an external capsule/label scanner-defect detection system 205 measures and detects defects such as bubbles, wrinkles, or an uneven application of the heat-shrink/roll-on capsule 271 and the label 281. The external capsule/label scanner-defect detection system 205 also detects fish eyes that form due to moisture trapped under the capsule along with other defects such as burn marks or holes in the heat-shrink or roll-on capsule 271. In certain embodiments, during production of the beverage package the capsule/label scanner-defect detection system 205 scans the product label 281 for defects, such as wrinkles, scuffing, incorrect position, incorrect orientation, and flagging-edges, which can result from raw material or process issues. If defects exceed acceptable quality limits on the package, the package is sent to package rejects 288. During setup or troubleshooting the present bottle 210 is transported to finished goods packaging 290. All information regarding package defects can be sent to the user real-time and stored for future review including modelling. This information could include the number of rejects, the rate of rejects and the percent of total production rejected at any time.

The finished goods packaging 290 involves moving the present bottle 210 from the labeller 280 to packaging, which can include placing the finished product into a corrugated cardboard box. In certain embodiments, the present bottle 210 measures vibration and g-force data using internal 3-axis accelerometers 317 to detect excessively rough handling in the finished goods packaging 290 area. Data showing excessively rough handling would indicate that the system is set-up incorrectly, is malfunctioning, or the control parts are worn/broken.

FIG. 3 depicts an exemplary sensor bottle 300, according to one embodiment. The present bottle 300 has an outer layer 301 that can be made using various metals and plastics placed in strategic locations to withstand the rigors of commercial bottling systems. According to one embodiment, outer layer 301 is plastic to facilitate the wireless sending of data generated from the sensors on the bottle and the reading of ultra-high frequency (UHF) radio frequency identification (RFID) tags located on unit operations, such as, capper heads, cork locks, and turret positions plus strategic locations throughout the bottling line allowing the bottle to send location data along with associated process data to feed through analytics models to generate recommendations to users. This data can be used to determine areas of the bottling line, and settings for specific units, that need attention. The present bottle 300 measures and collects data for set-ups, set-up confirmations, troubleshooting, and predictive maintenance in bottling line unit operations and systems. For example, temperature, pressure, and chemical data can be measured, collected, and transmitted for analysis, as described in more detail below.

In one embodiment, the present bottle 300 includes several sensors for data collection purposes, such as an external bottle top temperature sensor 310, which measures the temperature distribution on top of the bottle, and an internal temperature sensor located in the reservoir tube 430 that measures the temperature of the contents of the bottle, for example the temperature of a rinse solution and/or beverage. The present bottle 300 includes an internal pressure sensor 320 that collects data on internal pressures created by the rinser, filler, and the beverage after the closure is applied. In certain embodiments, a force sensor or sensors 392 on the bottom of the bottle measure the top load force applied on the bottle 300, for example the force applied by a filler or a capper head. The present bottle 300 includes a chemical sensor 330 in the lower portion of the reservoir tube 430, which measures, for example, acidity, sugars, alcohol, oxygen and $CO_2$ concentrations of the liquid in the bottle, and a chemical sensor 330 in the upper portion of the reservoir tube 430 that measures the levels of various gasses in the bottle's headspace, such as oxygen, and $CO_2$. In certain embodiments, the present bottle 300 includes a 3-axis accelerometer 317, which can measure and detect the movement of the bottle, and also detect if the bottle has experienced excessive shocks due to impact with control parts or bottling line components that are worn or out of alignment. In certain embodiments, the present bottle 300 includes a vacuum/pressure sensor 350, which can detect faults such as no or inadequate vacuum, high headspace pressure, leaks or other defects that may occur in the capping or corking bottling line systems.

The present bottle 300 includes a data acquisition/signal conditioner 360 such as an MSR model 43. In certain embodiments, the data acquisition/signal conditioner 360 can internally measure and record conditions such as temperature, humidity, light, pressure, and acceleration, and is equipped to perform such measurements simultaneously with each data point time and date stamped. According to one embodiment, the data acquisition/signal conditioner 360 also has 8 analog input channels capable of sampling at a rate of 1024 hertz. In another embodiment, data acquisition/signal conditioner 360 samples at rates exceeding 1 million samples per second. In another embodiment, the data acquisition/signal conditioner 360 has more than 8 analog input channels and can include a number of digital inputs. These analog inputs can include voltage or amperage readings from a variety of sensors including force sensing resistors, load cells, chemical, proximity, location, temperature, etc. Digital inputs can include data streams describing a device's address and description. In certain embodiments, the data acquisition and signal conditioner 360 has a built-in transmission wireless device, such as a Bluetooth or WiFi system 361, for transmitting data such as temperature, humidity, light, pressure, force, chemical and acceleration or any variety of digital data such as capper head identification, to a storage and data management device, such as a cloud server (e.g., data gateway and collection/analytics server 362) for review, analysis, and user recommendation generation. In another embodiment, the data transmission occurs via a wired connection 363 to a data collection and analytics server 364 or 630.

The present bottle 300 includes an output module 370, which can be equipped with indicator lights 371 and a display 372 to relay information such as proper bottle operation, and faults. In certain embodiments, if the output module 370 detects a fault, it automatically requests a new bottle via communication to the bottling line set-up, confirmation, troubleshooting owner 660 and includes transmission of shipping return information for the defective bottle.

The present bottle 300 includes a power source and regulation device 380. In certain embodiments, the power source is a rechargeable battery, for example, a rechargeable lithium battery 381. In one embodiment, the rechargeable lithium battery 381 can charge wirelessly when placed on charging base 382, which is connected to an AC power source 383.

The present bottle 300 also includes an ultra-high frequency (UHF) radio frequency identification (RFID) reader 393. RFID reader 393 works with UHF RFID tags placed on each component (and subcomponent) in system 100 and system 200. For example, an RFID tag may be placed on each capper head of capper system 160 to identify individual capper heads and on each turret location of capper system 160 to identify the individual capper head's location allowing the sensor readings to be associated with a particular capper head and location. RFID tags may also be read from the corker heads and corker turret locations of corker system 260.

The present bottle 300 may also have grooves 394 on its upper neck matching the target thread and pilfer roller positions for aiding a mechanic when adjusting the roller positions on capper heads. In addition, the present bottle 300 has bearings 395 at the top of the neck and bearings 396 at the bottom of the bottle to allow the mechanic the ability to easily rotate bottle 300 when under a capper head on a set-up device or a capper head installed on a turret in a process such as shown in system 100.

Figure 4:
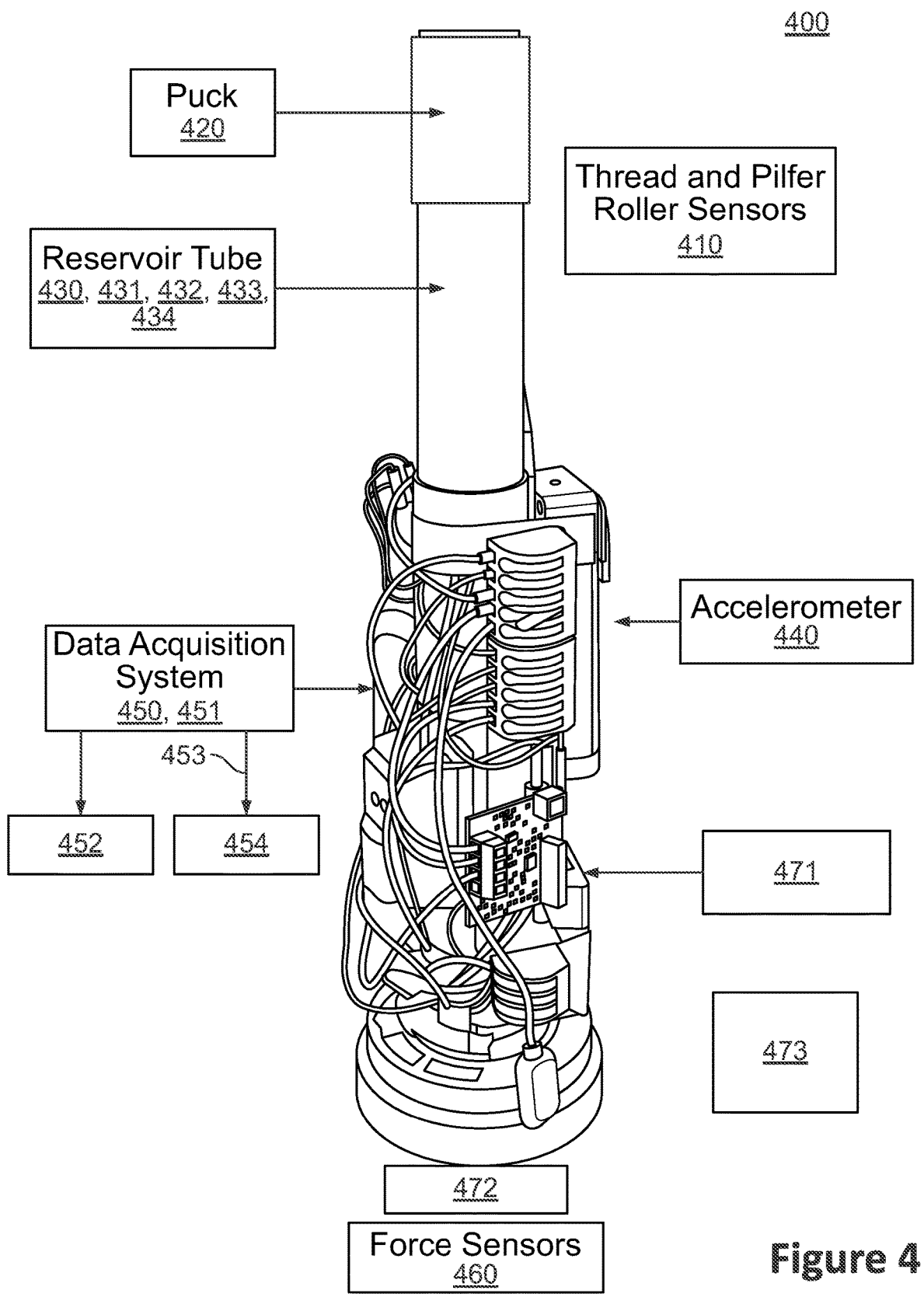
FIG. 4 depicts an exemplary sensor bottle, according to one embodiment.

FIG. 4 depicts an exemplary sensor bottle 400, according to one embodiment. The present bottle 400 has an outer layer (not shown) made of a metal, such as stainless steel and aluminium, to withstand the rigors of a commercial bottling line filler and capper. The present bottle 400 allows for data collection for capper head set-up, capper head set-up confirmation through the capper turret at production speeds, troubleshooting during a commercial bottling run, and data generation for the development of analytics models for predictive maintenance, for example g-force data, pressure data, and position data, and transmits that data either wired or wirelessly for analysis, as described in more detail below. According to another embodiment, the outer layer 401 is made using a suitably durable plastic or plastic/metal combination.

In one embodiment, the present bottle 400 includes several force sensors. The present bottle 400 includes thread and pilfer roller sensors 410, for example, Tekscan Flexi-Force 100 lb. force sensors. The thread and pilfer roller sensors 410 detect thread and pilfer roller forces, to ensure that the thread and pilfer rollers will create quality threads and pilfer tucks, respectively. If the thread force is too high, the rollers might cut through the cap metal and if too low, the threads might not be rolled into the bottle's threads deep enough, leading to a defect called "spinners" where the cap's threads strip before the bridges break during package opening resulting in the cap remaining on the bottle and spinning in place. If the pilfer force is too high, the roller might cut through the cap metal or cause the cap bridges to break and if too low might not tuck the pilfer deep enough leading to a defect called "lifters" where the entire cap skirt lifts off of the bottle during opening and the cap's bridges never break. If this happens, it becomes difficult to detect whether the bottle has been tampered with because someone could remove the entire cap skirt, tamper with the contents, and then replace the cap skirt without detection.

The present bottle 400 can include a puck 420, which is a stainless steel disc within the neck of the bottle that covers the thread and pilfer roller force sensors 410. In certain embodiments, there are two or more pucks 420, one or more that covers the thread roller force sensor, and one that covers the pilfer roller force sensor.

Figure 10A:
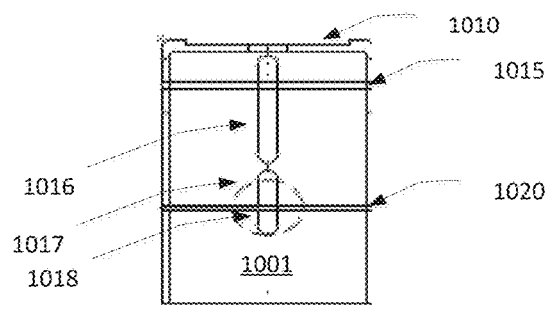
FIG. 10A illustrates a front view of removable sensor cap, according to one embodiment.
Figure 10B:
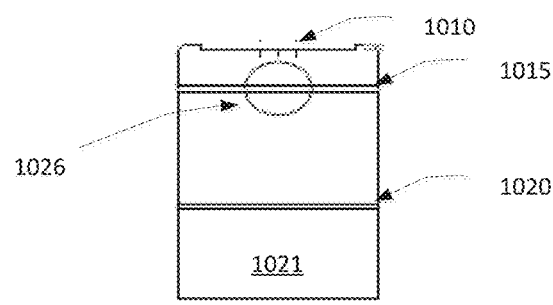
FIG. 10B illustrates a side view of removable sensor cap, according to one embodiment.

Sensor bottle 400 may have a removable sensor cap that houses a puck 420 and thread and pilfer roller sensors 410. FIG. 10A illustrates a front view of removable sensor cap 1001, according to one embodiment of a bottle designed to assist mechanics in setting up capper heads. Removable sensor cap 1001 has an inset 1010 to receive a removable top insert that may contain a bearing that allows the bottle top to rotate freely when under a compressive load, typically experienced when a capper head is lowered onto the bottle for set-up or testing. Removable sensor cap 1001 has a groove acting as a thread roller location guide 1015 and another groove acting as a pilfer roller location guide 1020 allowing the mechanic to accurately adjust the rollers to the proper height. Removable sensor cap 1001 has position sensors 1016 and 1018 that measures the thread and pilfer roller positions, respectively, using a voltage divider sensor that outputs an analog signal relative to the thread and pilfer roller contact locations. This allows for the sensor bottle 400 to collect and send roller position data to a storage device for real-time or retrospective review and analysis. Puck 1017 sits over the pilfer roller force sensing resistor sensor on the backside of the cap 1001. This pilfer roller force sensor system allows for the force data to be collected and sent for real time or retrospective review and analysis. FIG. 10B illustrates a side view of removable sensor cap 1021, according to one embodiment. Removable sensor cap 1021 has a puck 1026 that sits over one of two thread roller force sensing resistor sensors. This thread roller force sensor system allows for the force data to be collected and sent for real time or retrospective review and analysis.

Figure 10C:
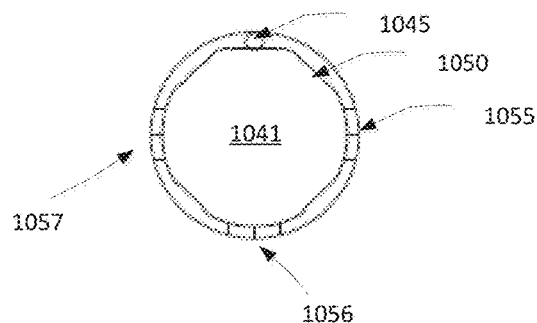
FIG. 10C illustrates a top view of removable sensor cap, according to one embodiment.

FIG. 10C illustrates a top view of removable sensor cap 1041, according to one embodiment. Shown in the top view 1041 are the thread and pilfer roller position sensor contact rubber 1045, thread roller puck 1055, thread roller puck 1057, and pilfer roller puck 1056. Thread roller puck 1055 and thread roller puck 1057 may be vertically offset to capture the maximum amount of force data as the thread roller moves from the top of the cap 1041 towards the bottom of the cap 1041 during a capping event. The surface is flat under thread and pilfer roller position sensor contact rubber 1045 to ensure accurate readings from the position sensor. The surfaces under pucks 1055-1057 may be curved to ensure accurate readings from their respective force sensors. The cap 1001 interior profile 1050 is designed to ensure the cap 1001 is properly aligned when placing it onto bottle 400 and to allow the cap to resist rotation when the capper head thread and pilfer rollers are spun around its circumference.

Figure 10D:
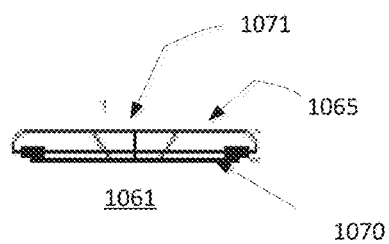
FIG. 10D illustrates a side view of removable top insert for the removable sensor cap, according to one embodiment.

FIG. 10D illustrates a side view of removable top insert 1061, according to one embodiment. Removable top insert 1061 mimics a commercial glass bottle's finish and the lower portion 1070 is designed to align with and securely fit into the depression 1010 of the sensor cap 1001. The top surface 1065 of the removable top insert 1061 can be made using oil impregnated brass to allow for easier rotation of bottle 400 when under typical capper head top loads. Top surface 1065 may also be fitted with bearings to further reduce the torque required to rotate the bottle 400 when under typical capper head top loads. Top surface 1065 may also include an indentation 1071 to accommodate a screw to secure the removable top insert 1061 to the removable cap 1001. Other mechanisms may be used to secure the removable top insert 1061 to the removable cap 1001.

The present bottle 400 includes a reservoir tube 430 that receives a rinse solution from the bottle rinser and/or a beverage, such as wine, from the bottling line filler. In certain embodiments, the reservoir tube 430 includes a sensor 431 that measures the headspace pressure. The reservoir tube 430 can have chemical sensors 432 at the top and bottom of the tube that are scanned by a reader 433, to determine chemical properties, such as the oxygen concentration of the contents of the present bottle 400. The chemical sensor reader 433 might also measure the pH of the contents of the present bottle 400. In certain embodiments the reservoir tube 430 includes a temperature sensor 434 to measure the temperature of the liquid contents of the present bottle 400.

In certain embodiments, the present bottle 400 includes an 3-axis accelerometer 440. The accelerometer 440 is an electromechanical device that can measure and detect the movement of the bottle, and also detect if the bottle has experienced excessive physical impacts due to misaligned, excessively worn, or broken bottling line components. This vibration data can be stored along with bottle location data for analysis using various analytics techniques in order to interpret vibration patterns and to provide the user with advice concerning any actions that need to be taken to ensure the line is being maintained and set-up properly.

In one embodiment, the present bottle 400 includes a data acquisition and signal conditioner 450. In certain embodiments, the data acquisition and signal conditioner 450 can measure and record temperature, humidity, light, pressure, and acceleration, and is equipped to perform such measurements simultaneously. In certain embodiments, the data acquisition and signal conditioner 450 has a built-in transmission wireless device, such as a Bluetooth or WiFi system 451, for transmitting recorded data such as temperature, humidity, light, pressure, acceleration, and any sensor data from the analog input channels to a cloud server 452 for review, analysis, and recommendation generation. In another embodiment, the data transmission occurs via a wired connection 453 to a server 454.

The present bottle 400 includes top load force sensors 460 on the bottom of the bottle. In one embodiment, the present bottle 400 has four Tekscan 1001*b* top load force sensors configured to measure total loads as high as 700 pounds 460. In another embodiment, the force is measured by a load cell set-up to measure top loads as high as 700 lbs. In certain embodiments, the pressure of the top load force is measured by the top load force sensors 460, and the force data is analyzed to help ensure the proper filling and cap application conditions are being met.

The present bottle 400 includes a power source and regulation device (not shown). In certain embodiments, the power source is a rechargeable battery, for example, a rechargeable lithium battery 471 inside the data acquisition system housing. In one embodiment, the rechargeable lithium battery 471 can charge wirelessly when placed on charging base 472, which is connected to an AC power source 473.

Figure 5:
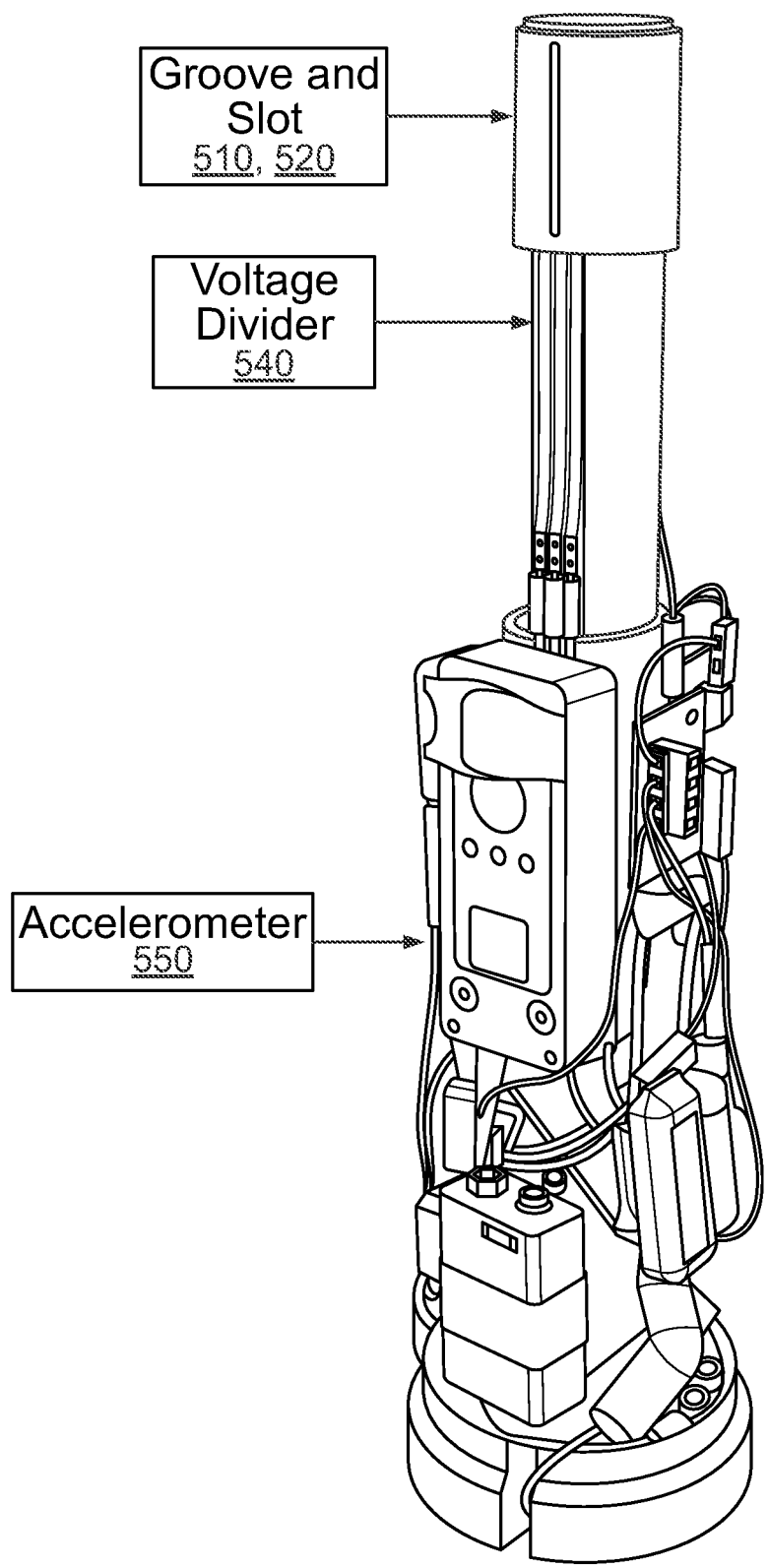
FIG. 5 depicts an exemplary sensor bottle, according to one embodiment.

FIG. 5 depicts an exemplary sensor bottle 500, according to one embodiment. The present bottle 500 has an outer layer 501 made of a metal, such as stainless steel, to withstand the pressures of the capper rollers of the bottling systems. The present bottle 500 allows for capper head set-up, capper head set-up confirmation at production speeds through the capper turret, troubleshooting during a commercial bottling run, and development of analytics models for predictive maintenance. For example temperature data, pressure data, and chemical data are collected by the sensor bottle 500 which then transmits that data for analysis, as described in more detail below.

In certain embodiments, the present bottle 500 has a groove and slot 510, 520 for the insertion of an elastic piece, such as rubber, that is pushed into the voltage divider 540, for example, a Tekscan FlexiPot strip position sensor, by thread or pilfer rollers passing over it. When the voltage divider is touched by the deflected rubber piece, a voltage is generated that can be correlated to a position relative to a datum, such as the top of the present bottle 500. The position of thread and pilfer rollers is important for the proper application of a screw cap and this data can help ensure that the screw-cap thread-start is proper and that the pilfer rollers are contacting the proper location of the cap for the specific bottle finish. The electronic data from the voltage divider can be directly sent through predictive models at the edge network to generate immediate recommendations to the user and can also be stored for later use.

In certain embodiments, the present bottle 500 includes an accelerometer 550. The accelerometer 550 is an electromechanical device that can measure movement of the bottle, and also detect if the bottle has experienced excessive physical impacts due to misaligned, excessively worn, or broken bottling line components or other shocks. Data from the accelerometers can be sent through predictive models for immediate feedback to the user. This feedback could include warnings and recommendations regarding control part settings/adjustments, warnings regarding excessive wear on control parts, recommendations for worn parts that likely need replacing, and requests to order spare parts or preventative maintenance services to help ensure that the line is serviced before a breakdown occurs.

FIG. 6 depicts an exemplary network that converts and sends data at the edge, collects data, analyzes data, and generates recommendations to the bottle user, according to one embodiment. Network system 600 collects and analyzes data transmitted by a bottle with sensors and a bottling line defect detection system taking various measurements and collecting data from equipment and materials used in bottling line systems. A data acquisition rate suitable for allowing the analytic models to provide accurate predictions and recommendations to the user at the right time will be specified and used (e.g., 1000 Hz).

In certain embodiments, the network system 600 may be a wired or wireless communication network, and can utilize edge network computing and feedback for high speed response, including responses fast enough to send signals to a commercial process for automatic adjustments to process setpoints, and cloud computing technology for model refinement and data storage over the Internet. The network system 600 includes a data gateway and collection/analytics server 630, which can provide feedback directly to the bottling process or user immediately regarding bottle sensor data 611 and bottling line defect detection data 621 and can collect and store this same data for future use. The data collection and analytics server can combine the data from these two sources for more detailed predictive model creation and better prescriptive analytics for packaging line user recommendations.

The data collection and analytics server 630 evaluates the bottle sensor data 611 and scanner bottling line defect detection data 621 to detect potential faults in equipment and/or raw materials in the bottling line systems, and allows for both automatic and user-initiated processes to resolve the faults, and also increase efficiency. In a certain embodiment, the data gateway and collection/analytics server 630 may, for example, upon detecting a fault in the bottling line system, automatically transmit a process setting adjustment command to the bottling line system allowing for an automatic line adjustment to correct a fault. In another embodiment, the data collection and analytics server 630 may, for example, alert users to potential faults by communicating wirelessly with a user device dashboard 650 and a bottling line set-up, confirmation, troubleshooting owner system 660, which may be part of a cloud computing platform.

The user device dashboard 650 and a bottling line set-up, confirmation, troubleshooting owner 660 system may be computing devices such as personal computers, laptops, PDAs, smartphones, tablets, or any other devices that can be used to communicate with a given network, and may use edge network and/or cloud computing technology. Users may participate in various activities, including using the data in the data collection and analytics server 630 to manually make the recommended bottling line equipment adjustments in response to fault alerts detected by the system. The alerts received by the bottling line set-up, confirmation, troubleshooting owner 660 may also be sent directly to the sensor bottle users. It can also allow the bottling line set-up, confirmation, troubleshooting owner 660 to observe the bottling line customer setting up the bottling line components such as capper heads, observe the confirmation run data along with any troubleshooting runs in order to intervene with the customer as necessary. This intervention could be in the form of a text, email, or phone call and could be initiated by the system or a person.

Figure 7:
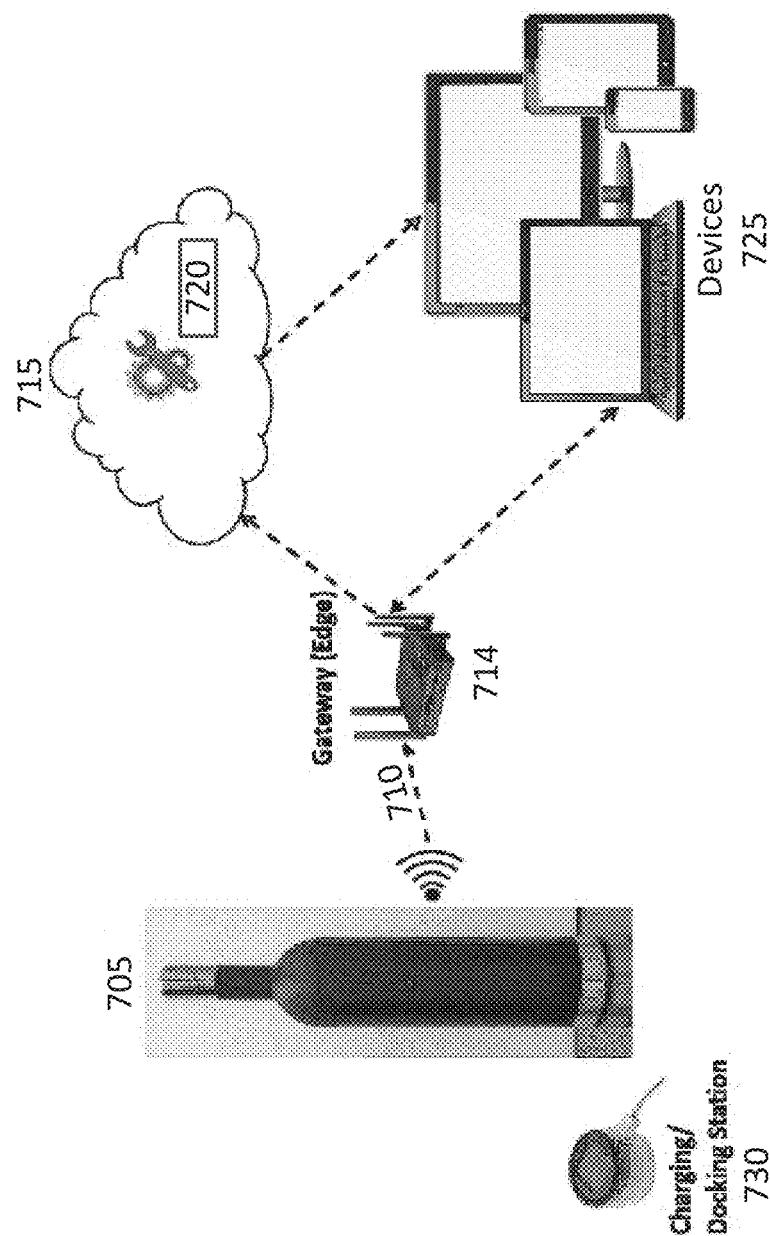
FIG. 7 depicts an exemplary network that collects and analyzes data, according to another embodiment.

FIG. 7 depicts an exemplary network that collects and analyzes data, according to another embodiment. According to one embodiment, system 700 includes a bottle 705, such as the present bottles 110, 210, or 300 that use a wireless link 710 to communicate with a gateway 714 and cloud repository 715. According to one embodiment, defect systems (e.g., defect systems 102, 104, 105, 202, 204, 205, etc.) also communicate with a gateway 714 and cloud repository 715 via a communications link 710, which may be wired or wireless. In addition, defect systems and bottle 705 may communicate directly with customer data devices 725 through the gateway 714 over a wireless or wired communications link 710. According to another embodiment, customer data devices 725 may be maintained and operated by a third party responsible for deploying bottle 705. A data analyzer server 720 that may reside in the cloud repository 715 analyzes the data stored in the cloud repository that is derived from the present bottle 705. The data analyzer server 720 communicates with customer data devices 725, which may include laptops, tablets, desktops, and mobile phones. The present bottle 705 also may be charged using charging/docking station 730.

Figure 8:
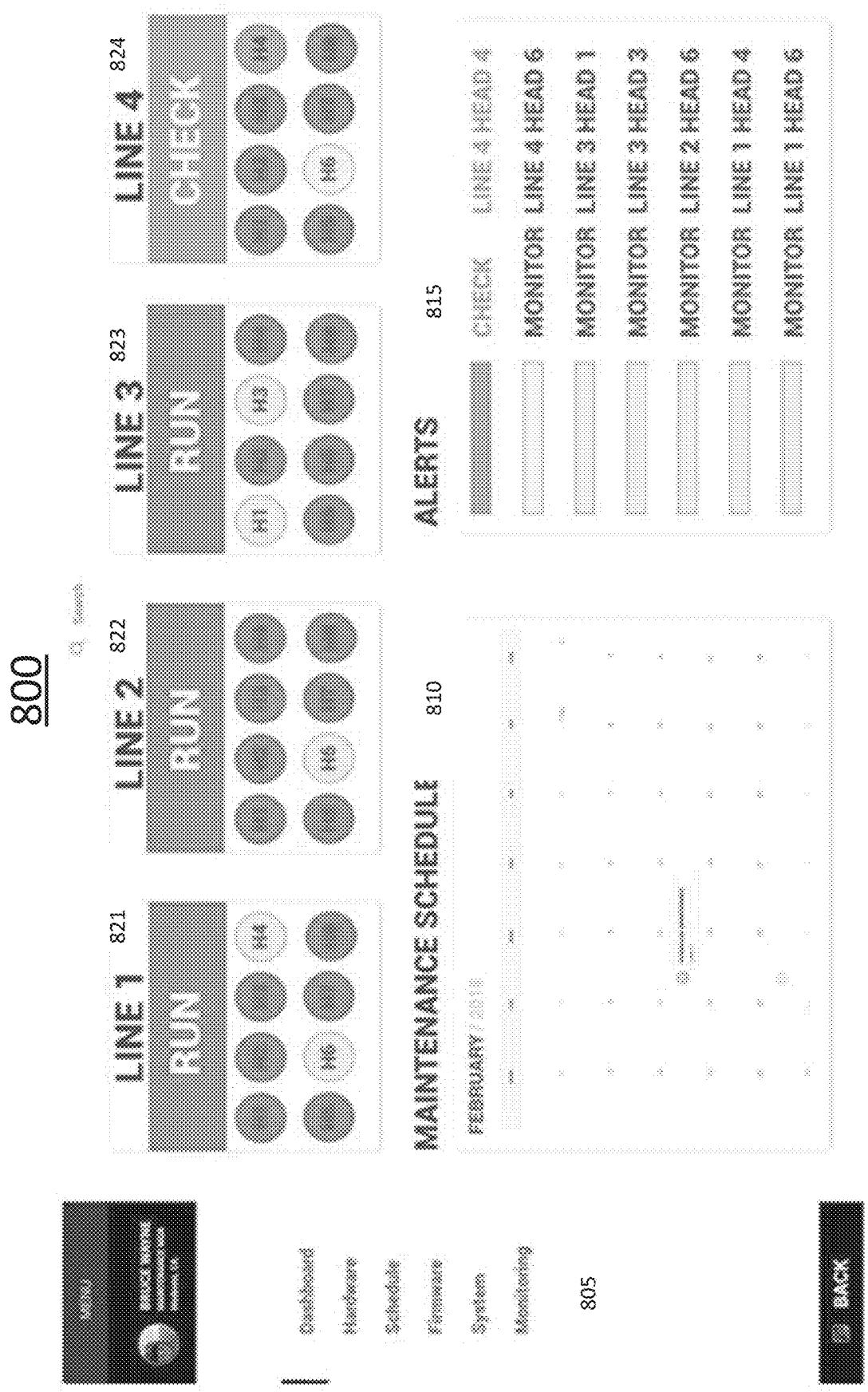
FIG. 8 depicts an exemplary dashboard that allows a user to manage a bottling system, according to one embodiment.

FIG. 8 depicts an exemplary dashboard that allows a user to manage a bottling system, according to one embodiment. Dashboard 800 contains information and data provided by the gateway 714, data analyzer server 720 or data collection and analytics server 630. The data may include bottle sensor data, bottling line defect detection data, and data from process equipment and PLC's. Dashboard 800 includes a number of menus 805, including hardware, schedule, firmware, system, and monitoring. Dashboard 800 further includes status information for four bottling lines 821-824 with color coded status indicators. For example, line 4 may have a problem with head 4 (H4). Alerts 815 indicate that the user should check line 4 head 4 and monitor other lines and heads. Dashboard 800 also includes a maintenance schedule 810 for components on the bottling line.

Figure 9:
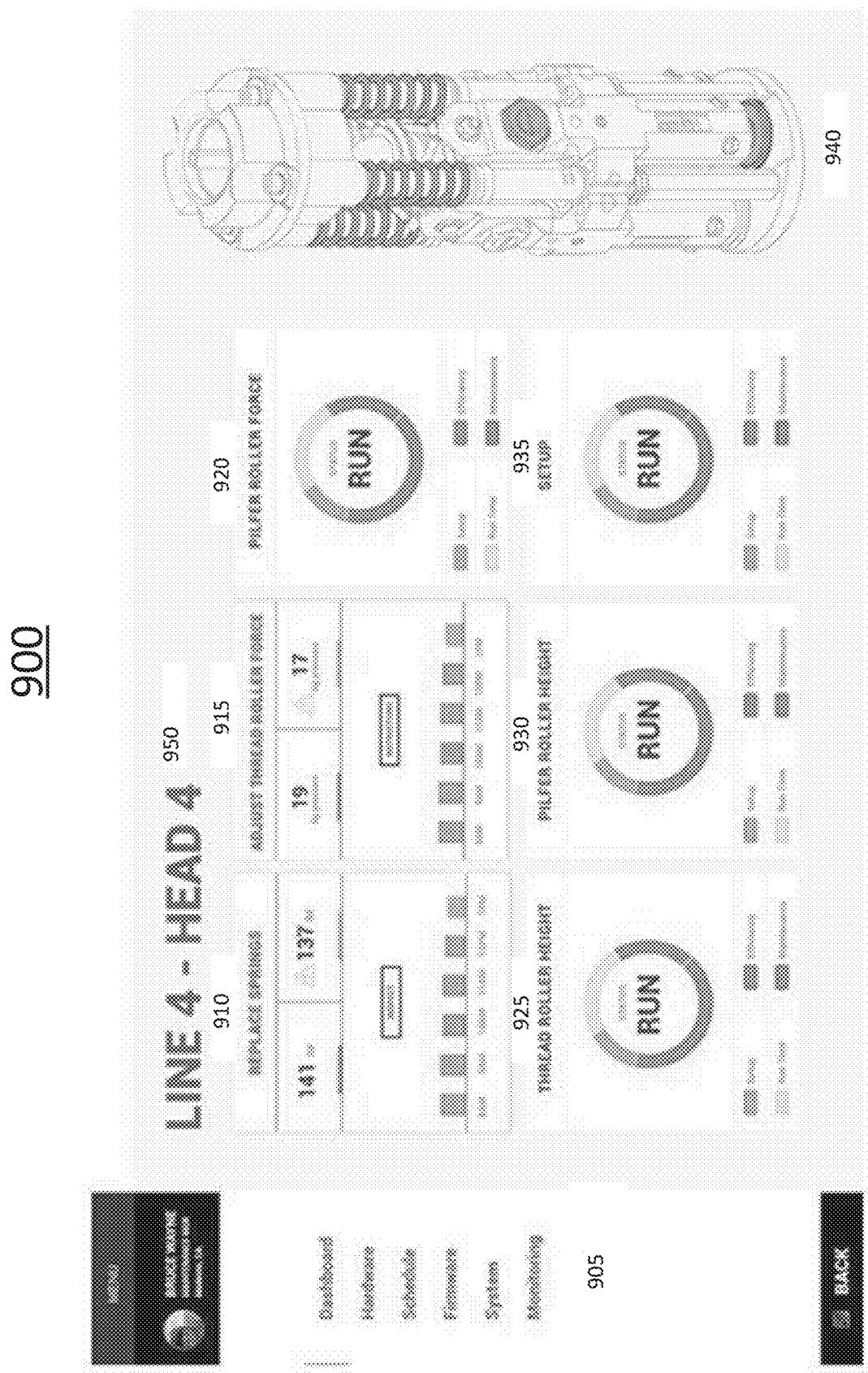
FIG. 9 depicts an exemplary dashboard that allows a user to monitor a bottling system's performance, according to one embodiment.

FIG. 9 depicts an exemplary dashboard that allows a user to monitor a bottling system's performance, according to one embodiment. Dashboard 900 includes a menu 905 with information regarding hardware, schedule, firmware, system and monitoring. Dashboard 900 identifies the location of a problem 950 as line 4, head 4. The dashboard communicates that there are two issues with head 4 on line 4. The thread roller force needs to be adjusted 915 from 17 to 19 pounds and the top load needs to be adjusted 910 from 137 to 141 pounds. The dashboard includes a diagram of the capper head 940 highlighting the screw that needs adjusting and the potentially problematic springs that should be replaced. The dashboard 900 indicates that other parameters are working within acceptable parameters, such as pilfer roller force 920, thread roller height 925, pilfer roller height 930, and setup 935.

In addition to the information illustrated in dashboards 800 and 900, the present system can determine whether bottling line systems are functioning within an acceptable operating range. For example, as discussed above, the present bottle can measure the top load applied by capper system 160 (e.g., 396) and data analyser 720 feeds the top load data into predictive models that can inform the appropriate users if the product quality is likely to move outside of acceptable range. The gateway 714 can compare the top load force against a recommended top load value to alert an appropriate user whether the force is within an acceptable operating range (e.g., within 5% of the recommended value). A dashboard may be used to inform the user whether the measurement is within the operating range. This approach can be used with any of the sensor data generated from the sensor bottles 300, 400, 500 or 705.

One of ordinary skill in the art will appreciate that not all bottling line systems will have all these components and may have other components in addition to, or in lieu of, those components mentioned here. Furthermore, while these components are viewed and described separately, various components may be integrated into a single unit in some embodiments.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention.

What is claimed is:

1. A bottle, comprising:
   an outer layer;
   a reservoir tube inside the outer layer that connects a reservoir inside the outer layer to a neck of the bottle;
   a battery inside the outer layer; and
   one or more sensors powered by the battery for collecting data from a bottling line process,
   wherein the reservoir tube is configured to receive at least one of a rinse solution or a beverage during the bottling line process.

2. The bottle of claim 1, wherein the one or more sensors includes an internal temperature sensor located in the reservoir tube that measures a temperature of fluid in the bottle.

3. The bottle of claim 1, wherein the one or more sensors includes an external bottle top temperature sensor that measures a temperature distribution on top of the bottle.

4. The bottle of claim 1, wherein the one or more sensors includes an internal pressure sensor that measures internal pressures created in the bottle by at least one of a rinser, a filler, and a closure application.

5. The bottle of claim 1, wherein the one or more sensors includes a force sensor on a bottom of the bottle that measures a top load force applied on the bottle, the top load force applied by a filler or a capper head.

6. The bottle of claim 1, wherein the one or more sensors includes a chemical sensor in the reservoir tube that measures one or more of acidity, sugars, alcohol, oxygen, or carbon dioxide concentrations of fluid in the bottle.

7. The bottle of claim 1, wherein the one or more sensors includes a chemical sensor that measures levels of gasses in a headspace, the gasses including one or more of oxygen or carbon dioxide.

8. The bottle of claim 1, wherein the one or more sensors includes a 3-axis accelerometer that measures and detects movement of the bottle, and also detects shocks due to impact with bottling line components that are improperly set, wearing, or defective.

9. The bottle of claim 1, wherein the one or more sensors includes a vacuum/pressure sensor that detects faults including one or more of inadequate vacuum, high headspace pressure, or leaks that may occur in bottling line systems.

10. The bottle of claim 1, further comprising a data acquisition and signal conditioner to measure conditions including one or more of temperature, humidity, light, pressure, force, gas chemistry, liquid chemistry, or acceleration.

11. The bottle of claim 1, wherein the one or more sensors includes a force sensing resistor, a voltage divider, a load cell, a pressure transducer, a chemical sensor, a proximity sensor, a location sensor, or a temperature sensor.

12. The bottle of claim 10, wherein the data acquisition and signal conditioner communicates with a wireless transmission device to send data including one or more of temperature, humidity, light, pressure, force, chemical, or acceleration along with digital data including one or more of addresses, locations, or names.

13. The bottle of claim 1, wherein the bottle sends data to a data collection server and analytics server.

14. The bottle of claim 1, further comprising an output module that has indicator lights and a display.

15. The bottle of claim 1, wherein the battery can charge wirelessly when placed on a charging base.

16. The bottle of claim 1, further comprising a radio frequency identification (RFID) reader for reading one or more RFID tags on components in the bottling line process.

17. The bottle of claim 1, further comprising grooves on the neck used to configure one or more capper head rollers.

18. The bottle of claim 1, further comprising top bearings around a top of the neck of the bottle.

19. The bottle of claim 1, further comprising bottom bearings at a bottom edge of the bottle.

20. A method comprising:
    providing a bottle comprising:
      an outer layer;
      a reservoir tube inside the outer layer that connects a reservoir inside the outer layer to a neck of the bottle;
      a battery inside the outer layer; and
      one or more sensors powered by the battery;
    inserting the bottle into a bottling line process;
    collecting data from the bottling line process using the one or more sensors; and
    receiving at least one of a rinse solution or a beverage in the reservoir tube during the bottling line process.

21. A system comprising:
    a bottle comprising:
      an outer layer;
      a reservoir tube inside the outer layer that connects a reservoir inside the outer layer to a neck of the bottle;
      a battery inside the outer layer; and
      one or more sensors powered by the battery; and
    equipment for performing a bottling line process,
      wherein the bottle is inserted into the bottling line process and data is collected from the bottling line process using the one or more sensors, and wherein at least one of a rinse solution or a beverage is received in the reservoir tube during the bottling line process.

\* \* \* \* \*